United States Patent
Olsen et al.

(10) Patent No.: US 7,579,177 B2
(45) Date of Patent: Aug. 25, 2009

(54) ALCOHOL PRODUCT PROCESSES

(75) Inventors: Hans Sejr Olsen, Holte (DK); Barrie Edmund Norman, Birkerod (DK); Mogens Wumpelmann, Herlev (DK); Jeppe Wegener Tams, Gentofte (DK)

(73) Assignee: Novozymes A/S, Bagsvaerd (DK)

( * ) Notice: Subject to any disclaimer, the term of this patent is extended or adjusted under 35 U.S.C. 154(b) by 248 days.

(21) Appl. No.: 10/558,552

(22) PCT Filed: May 28, 2004

(86) PCT No.: PCT/DK2004/000373

§ 371 (c)(1),
(2), (4) Date: Nov. 28, 2005

(87) PCT Pub. No.: WO2004/106533

PCT Pub. Date: Sep. 12, 2004

(65) Prior Publication Data

US 2007/0031952 A1    Feb. 8, 2007

Related U.S. Application Data

(60) Provisional application No. 60/474,880, filed on May 30, 2003.

(30) Foreign Application Priority Data

May 30, 2003  (DK)  ................ 2003 00812

(51) Int. Cl.
  *C12P 7/14*  (2006.01)
  *C12P 7/06*  (2006.01)
  *C12N 9/24*  (2006.01)
  *C12N 9/28*  (2006.01)
  *C12N 9/44*  (2006.01)

(52) U.S. Cl. .............. 435/162; 435/161; 435/200; 435/202; 435/203; 435/210

(58) Field of Classification Search ............ 435/161; 426/11
See application file for complete search history.

(56) References Cited

U.S. PATENT DOCUMENTS

| 4,234,686 A | * | 11/1980 | Marshall | ............. 435/94 |
| 4,316,956 A | | 2/1982 | Lutzen | |
| 4,318,927 A | * | 3/1982 | Marshall | ............. 426/11 |
| 4,318,989 A | * | 3/1982 | Marshall | ............. 435/205 |
| 7,244,597 B2 | * | 7/2007 | Veit et al. | ............. 435/161 |

FOREIGN PATENT DOCUMENTS

| EP | 0140410 | 5/1985 |
| EP | 0171218 | 2/1986 |
| WO | WO 00/29560 | 5/2000 |
| WO | WO 01/34784 | 5/2001 |
| WO | WO 02/38787 | 5/2002 |
| WO | WO 03/068976 | 8/2003 |
| WO | WO 2004/080923 | 9/2004 |
| WO | WO 2005/113785 | 12/2005 |

OTHER PUBLICATIONS

Seinosuke Ueda, TIBS, XP008022741, pp. 89 and 90 (1981).
Brady et al, American Chemical Society, Biochemistry, vol. 29, No. 26 pp. 6245-6249 (1990).
Takasaki et al, Journal of Fermentation and Bioengineering, vol. 77, No. 1, pp. 94-96 (1994).
Kaneko et al, Journal of Fermentation and Bioengineering, vol. 81, No. 4, pp. 292-298 (1996).
Takii et al, Appl Microbiol Biotechnology, vol. 44, pp. 629-634 (1996).

* cited by examiner

*Primary Examiner*—Herbert J. Lilling
(74) *Attorney, Agent, or Firm*—Elias Lambiris

(57) ABSTRACT

The present invention relates to processes for production of an alcohol product from granular starch comprising a pretreatment at an elevated temperature below the initial gelatinization temperature of said granular starch followed by simultaneous saccharification and fermentation.

24 Claims, No Drawings

SEQUENCE LISTING

<160> NUMBER OF SEQ ID NOS: 6

<210> SEQ ID NO 1
<211> LENGTH: 484
<212> TYPE: PRT
<213> ORGANISM: Aspergillus niger

<400> SEQUENCE: 1

```
Leu Ser Ala Ala Ser Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asn Glu Ile Tyr Cys Gly Gly Ser Trp Gln Gly Ile Ile Asp His
        35                  40                  45

Leu Asp Tyr Ile Glu Gly Met Gly Phe Thr Ala Ile Trp Ile Ser Pro
    50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
                85                  90                  95

Ala Asp Asn Leu Lys Ser Leu Ser Asp Ala Leu His Ala Arg Gly Met
            100                 105                 110

Tyr Leu Met Val Asp Val Val Pro Asp His Met Gly Tyr Ala Gly Asn
        115                 120                 125

Gly Asn Asp Val Asp Tyr Ser Val Phe Asp Pro Phe Asp Ser Ser Ser
130                 135                 140

Tyr Phe His Pro Tyr Cys Leu Ile Thr Asp Trp Asp Asn Leu Thr Met
145                 150                 155                 160

Val Glu Asp Cys Trp Glu Gly Asp Thr Ile Val Ser Leu Pro Asp Leu
                165                 170                 175

Asp Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Leu Glu Val Gln Pro Asp Phe Phe Pro Gly Tyr Asn Lys Ala Ser Gly
210                 215                 220

Val Tyr Cys Val Gly Glu Ile Asp Asn Gly Asn Pro Ala Ser Asp Cys
225                 230                 235                 240

Pro Tyr Gln Lys Val Leu Asp Gly Val Leu Asn Tyr Pro Ile Tyr Trp
                245                 250                 255

Gln Leu Leu Tyr Ala Phe Glu Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Lys Tyr
290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ala
                325                 330                 335

Gly Gly Lys Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ala Ala Asp Ser Ala Tyr Ile Thr Tyr Ala Asn
370                 375                 380

Asp Ala Phe Tyr Thr Asp Ser Asn Thr Ile Ala Met Ala Lys Gly Thr
385                 390                 395                 400

Ser Gly Ser Gln Val Ile Thr Val Leu Ser Asn Lys Gly Ser Ser Gly
                405                 410                 415
```

```
Ser Ser Tyr Thr Leu Thr Leu Ser Gly Ser Gly Tyr Thr Ser Gly Thr
                420                 425                 430

Lys Leu Ile Glu Ala Tyr Thr Cys Thr Ser Val Thr Val Asp Ser Ser
            435                 440                 445

Gly Asp Ile Pro Val Pro Met Ala Ser Gly Leu Pro Arg Val Leu Leu
        450                 455                 460

Pro Ala Ser Val Val Asp Ser Ser Ser Leu Cys Gly Gly Ser Gly Arg
465                 470                 475                 480

Leu Tyr Val Glu

<210> SEQ ID NO 2
<211> LENGTH: 514
<212> TYPE: PRT
<213> ORGANISM: Bacillus stearothermophilus

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
    290                 295                 300
```

```
Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp

<210> SEQ ID NO 3
<211> LENGTH: 483
<212> TYPE: PRT
<213> ORGANISM: Bacillus licheniformis

<400> SEQUENCE: 3

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160
```

```
Asp Gly Thr Asp Trp Asp Glu Ser Arg Lys Leu Asn Arg Ile Tyr Lys
            165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
            195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
            245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
            290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
            405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
            450                 455                 460

Glu Gly Trp Gly Glu Phe His Val Asn Gly Gly Ser Val Ser Ile Tyr
465                 470                 475                 480

Val Gln Arg

<210> SEQ ID NO 4
<211> LENGTH: 480
<212> TYPE: PRT
<213> ORGANISM: Aspergillus amyloliquefaciens

<400> SEQUENCE: 4

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45
```

-continued

```
Gln Ser Asp Asn Gly Tyr Gly Pro Tyr Asp Leu Tyr Asp Leu Gly Glu
     50                  55                  60
Phe Gln Gln Lys Gly Thr Val Arg Thr Lys Tyr Gly Thr Lys Ser Glu
 65                  70                  75                  80
Leu Gln Asp Ala Ile Gly Ser Leu His Ser Arg Asn Val Gln Val Tyr
                 85                  90                  95
Gly Asp Val Val Leu Asn His Lys Ala Gly Ala Asp Ala Thr Glu Asp
                100                 105                 110
Val Thr Ala Val Glu Val Asn Pro Ala Asn Arg Asn Gln Glu Thr Ser
            115                 120                 125
Glu Glu Tyr Gln Ile Lys Ala Trp Thr Asp Phe Arg Phe Pro Gly Arg
    130                 135                 140
Gly Asn Thr Tyr Ser Asp Phe Lys Trp His Trp Tyr His Phe Asp Gly
145                 150                 155                 160
Ala Asp Trp Asp Glu Ser Arg Lys Ile Ser Arg Ile Phe Lys Phe Arg
                165                 170                 175
Gly Glu Gly Lys Ala Trp Asp Trp Glu Val Ser Ser Glu Asn Gly Asn
            180                 185                 190
Tyr Asp Tyr Leu Met Tyr Ala Asp Val Asp Tyr Asp His Pro Asp Val
    195                 200                 205
Val Ala Glu Thr Lys Lys Trp Gly Ile Trp Tyr Ala Asn Glu Leu Ser
210                 215                 220
Leu Asp Gly Phe Arg Ile Asp Ala Ala Lys His Ile Lys Phe Ser Phe
225                 230                 235                 240
Leu Arg Asp Trp Val Gln Ala Val Arg Gln Ala Thr Gly Lys Glu Met
                245                 250                 255
Phe Thr Val Ala Glu Tyr Trp Gln Asn Asn Ala Gly Lys Leu Glu Asn
            260                 265                 270
Tyr Leu Asn Lys Thr Ser Phe Asn Gln Ser Val Phe Asp Val Pro Leu
    275                 280                 285
His Phe Asn Leu Gln Ala Ala Ser Ser Gln Gly Gly Gly Tyr Asp Met
290                 295                 300
Arg Arg Leu Leu Asp Gly Thr Val Val Ser Arg His Pro Glu Lys Ala
305                 310                 315                 320
Val Thr Phe Val Glu Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
    355                 360                 365
Thr Lys Gly Thr Ser Pro Lys Glu Ile Pro Ser Leu Lys Asp Asn Ile
370                 375                 380
Glu Pro Ile Leu Lys Ala Arg Lys Glu Tyr Ala Tyr Gly Pro Gln His
385                 390                 395                 400
Asp Tyr Ile Asp His Pro Asp Val Ile Gly Trp Thr Arg Glu Gly Asp
                405                 410                 415
Ser Ser Ala Ala Lys Ser Gly Leu Ala Ala Leu Ile Thr Asp Gly Pro
            420                 425                 430
Gly Gly Ser Lys Arg Met Tyr Ala Gly Leu Lys Asn Ala Gly Glu Thr
    435                 440                 445
```

```
Trp Tyr Asp Ile Thr Gly Asn Arg Ser Asp Thr Val Lys Ile Gly Ser
            450                 455                 460

Asp Gly Trp Gly Glu Phe His Val Asn Asp Gly Ser Val Ser Ile Tyr
465                 470                 475                 480
```

<210> SEQ ID NO 5
<211> LENGTH: 498
<212> TYPE: PRT
<213> ORGANISM: Aspergillus oryzae

<400> SEQUENCE: 5

```
Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
            20                  25                  30

Phe Leu Leu Thr Asp Arg Phe Ala Arg Thr Asp Gly Ser Thr Thr Ala
            35                  40                  45

Thr Cys Asn Thr Ala Asp Gln Lys Tyr Cys Gly Gly Thr Trp Gln Gly
        50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95

Asp Ala Tyr His Gly Tyr Trp Gln Gln Asp Ile Tyr Ser Leu Asn Glu
            100                 105                 110

Asn Tyr Gly Thr Ala Asp Asp Leu Lys Ala Leu Ser Ser Ala Leu His
        115                 120                 125

Glu Arg Gly Met Tyr Leu Met Val Asp Val Val Ala Asn His Met Gly
130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
        195                 200                 205

Asp Trp Val Gly Ser Leu Val Ser Asn Tyr Ser Ile Asp Gly Leu Arg
210                 215                 220

Ile Asp Thr Val Lys His Val Gln Lys Asp Phe Trp Pro Gly Tyr Asn
225                 230                 235                 240

Lys Ala Ala Gly Val Tyr Cys Ile Gly Glu Val Leu Asp Gly Asp Pro
                245                 250                 255

Ala Tyr Thr Cys Pro Tyr Gln Asn Val Met Asp Gly Val Leu Asn Tyr
            260                 265                 270

Pro Ile Tyr Tyr Pro Leu Leu Asn Ala Phe Lys Ser Thr Ser Gly Ser
        275                 280                 285

Met Asp Asp Leu Tyr Asn Met Ile Asn Thr Val Lys Ser Asp Cys Pro
290                 295                 300

Asp Ser Thr Leu Leu Gly Thr Phe Val Glu Asn His Asp Asn Pro Arg
305                 310                 315                 320

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350
```

-continued

```
Gln His Tyr Ala Gly Gly Asn Asp Pro Ala Asn Arg Glu Ala Thr Trp
        355                 360                 365

Leu Ser Gly Tyr Pro Thr Asp Ser Glu Leu Tyr Lys Leu Ile Ala Ser
        370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Asp Thr Thr Ile Ala Met
                405                 410                 415

Arg Lys Gly Thr Asp Gly Ser Gln Ile Val Thr Ile Leu Ser Asn Lys
                420                 425                 430

Gly Ala Ser Gly Asp Ser Tyr Thr Leu Ser Leu Ser Gly Ala Gly Tyr
            435                 440                 445

Thr Ala Gly Gln Gln Leu Thr Glu Val Ile Gly Cys Thr Thr Val Thr
        450                 455                 460

Val Gly Ser Asp Gly Asn Val Pro Val Pro Met Ala Gly Gly Leu Pro
465                 470                 475                 480

Arg Val Leu Tyr Pro Thr Glu Lys Leu Ala Gly Ser Lys Ile Cys Ser
                485                 490                 495

Ser Ser

<210> SEQ ID NO 6
<211> LENGTH: 555
<212> TYPE: PRT
<213> ORGANISM: Bacillus stearothermophilus

<400> SEQUENCE: 6

Met Lys Lys Thr Trp Lys Glu Gly Val Ala Tyr Gln Ile Tyr Pro
1               5                   10                  15

Arg Ser Phe Met Asp Ala Asn Gly Asp Gly Ile Gly Asp Leu Arg Gly
                20                  25                  30

Ile Ile Glu Lys Leu Asp Tyr Leu Val Glu Leu Gly Val Asp Ile Val
            35                  40                  45

Trp Ile Cys Pro Ile Tyr Arg Ser Pro Asn Ala Asp Asn Gly Tyr Asp
        50                  55                  60

Ile Ser Asp Tyr Tyr Ala Ile Met Asp Glu Phe Gly Thr Met Asp Asp
65                  70                  75                  80

Phe Asp Glu Leu Leu Ala Gln Ala His Arg Arg Gly Leu Lys Ile Ile
                85                  90                  95

Leu Asp Leu Val Ile Asn His Thr Ser Asp Glu His Pro Trp Phe Ile
                100                 105                 110

Glu Ser Arg Ser Ser Arg Asp Asn Pro Lys Arg Asp Trp Tyr Ile Trp
            115                 120                 125

Arg Asp Gly Lys Asp Gly Arg Glu Pro Asn Asn Trp Glu Ser Ile Phe
        130                 135                 140

Gly Gly Ser Ala Trp Gln Tyr Asp Glu Arg Thr Gly Gln Tyr Tyr Leu
145                 150                 155                 160

His Leu Phe Asp Val Lys Gln Pro Asp Leu Asn Trp Glu Asn Ser Glu
                165                 170                 175

Val Arg Gln Ala Leu Tyr Asp Met Ile Asn Trp Trp Leu Asp Lys Gly
                180                 185                 190

Ile Asp Gly Phe Arg Ile Asp Ala Ile Ser His Ile Lys Lys Lys Pro
            195                 200                 205

Gly Leu Pro Asp Leu Pro Asn Pro Lys Gly Leu Lys Tyr Val Pro Ser
        210                 215                 220
```

```
-continued

Phe Ala Ala His Met Asn Gln Pro Gly Ile Met Glu Tyr Leu Arg Glu
225                 230                 235                 240

Leu Lys Glu Gln Thr Phe Ala Arg Tyr Asp Ile Met Thr Val Gly Glu
                    245                 250                 255

Ala Asn Gly Val Thr Val Asp Glu Ala Glu Gln Trp Val Gly Glu Glu
                260                 265                 270

Asn Gly Val Phe His Met Ile Phe Gln Phe Glu His Leu Gly Leu Trp
            275                 280                 285

Lys Arg Lys Ala Asp Gly Ser Ile Asp Val Arg Arg Leu Lys Arg Thr
        290                 295                 300

Leu Thr Lys Trp Gln Lys Gly Leu Glu Asn Arg Gly Trp Asn Ala Leu
305                 310                 315                 320

Phe Leu Glu Asn His Asp Leu Pro Arg Ser Val Ser Thr Trp Gly Asn
                325                 330                 335

Asp Arg Glu Tyr Trp Ala Glu Ser Ala Lys Ala Leu Gly Ala Leu Tyr
            340                 345                 350

Phe Phe Met Gln Gly Thr Pro Phe Ile Tyr Gln Gly Gln Glu Ile Gly
        355                 360                 365

Met Thr Asn Val Gln Phe Ser Asp Ile Arg Asp Tyr Arg Asp Val Ala
        370                 375                 380

Ala Leu Arg Leu Tyr Glu Leu Glu Arg Ala Asn Gly Arg Thr His Glu
385                 390                 395                 400

Glu Val Met Lys Ile Ile Trp Lys Thr Gly Arg Asp Asn Ser Arg Thr
                405                 410                 415

Pro Met Gln Trp Ser Asp Ala Pro Asn Ala Gly Phe Thr Thr Gly Thr
            420                 425                 430

Pro Trp Ile Lys Val Asn Glu Asn Tyr Arg Thr Ile Asn Val Glu Ala
            435                 440                 445

Glu Arg Arg Asp Pro Asn Ser Val Trp Ser Phe Tyr Arg Gln Met Ile
450                 455                 460

Gln Leu Arg Lys Ala Asn Glu Leu Phe Val Tyr Gly Ala Tyr Asp Leu
465                 470                 475                 480

Leu Leu Glu Asn His Pro Ser Ile Tyr Ala Tyr Thr Arg Thr Leu Gly
                485                 490                 495

Arg Asp Arg Ala Leu Ile Ile Val Asn Val Ser Asp Arg Pro Ser Leu
            500                 505                 510

Tyr Arg Tyr Asp Gly Phe Arg Leu Gln Ser Ser Asp Leu Ala Leu Ser
        515                 520                 525

Asn Tyr Pro Val Arg Pro His Lys Asn Ala Thr Arg Phe Lys Leu Lys
        530                 535                 540

Pro Tyr Glu Ala Arg Val Tyr Ile Trp Lys Glu
545                 550                 555
```

ALCOHOL PRODUCT PROCESSES

CROSS-REFERENCE TO RELATED APPLICATIONS

This application is a 35 U.S.C. 371 national application of PCT/DK2004/000373 filed May 28, 2004, which claims priority or the benefit under 35 U.S.C. 119 of Danish application no. PA 2003 00812 filed May 30, 2003 and U.S. provisional application no. 60/474,880 filed May 30, 2003, the contents of which are fully incorporated herein by reference.

FIELD OF THE INVENTION

The present invention relates to processes for production of an alcohol product from granular starch comprising a pre-treatment at an elevated temperature below the initial gelatinization temperature of the granular starch followed by simultaneous saccharification and fermentation.

BACKGROUND OF THE INVENTION

Granular starch is found in grains, cereals or tubers of plants. The granular starch is in the form of microscopic granules, which are insoluble in water at room temperature. When an aqueous starch slurry is heated, the granules swell and eventually burst, dispersing the starch molecules into the solution. During this "gelatinization" process, there is a dramatic increase in viscosity. Because the solids level is 30-40% in a typical industrial process, the starch has to be thinned or "liquefied" so that it can be handled during the following process steps. This reduction in viscosity is generally accomplished by enzymatic degradation in a process referred to as liquefaction. During liquefaction, the long-chained starch is degraded into smaller branched and linear chains of glucose units (dextrins) by an alpha-amylase.

A conventional enzymatic liquefaction process may be carried out as a three-step hot slurry process. The slurry is heated to between 80-85° and thermostable alpha-amylase added to initiate liquefaction. The slurry is then jet-cooked at a temperature between 105-125° C. to complete gelatinization of the slurry, cooled to 60-95° C. and, generally, additional alpha-amylase is added to finalize hydrolysis. The liquefaction process is generally carried out at pH between 5 and 6. Milled and liquefied whole grains are known as mash.

During saccharification, the dextrins from the liquefaction are further hydrolyzed to produce low molecular sugars DP1-3 that can be metabolized by yeast. The hydrolysis is typically accomplished using glucoamylases, alternatively or in addition to glucoamylases, alpha-glucosidases and/or acid alpha-amylases can be used. A full saccharification step typically last up to 72 hours, however, it is common only to do a pre-saccharification of, e.g., 40-90 minutes at a temperature above 50° C., followed by a complete saccharification during fermentation in a process known as simultaneous saccharification and fermentation (SSF).

Fermentation, may be performed using a yeast, e.g., from *Saccharomyces* spp., which added to the mash. When the alcohol product is recovered ethanol, e.g. fuel, potable, or industrial ethanol, the fermentation is carried out, for typically 35-60 hours at a temperature of typically around 32° C. When the alcohol product is beer, the fermentation is carried out, for typically up to 8 days at a temperature of typically around 14° C.

Following fermentation, the mash may be used, e.g. as a beer, or distilled to recover ethanol. The ethanol may be used as, e.g., fuel ethanol, drinking ethanol, and/or industrial ethanol.

It will be apparent from the above discussion that the starch hydrolysis in a conventional alcohol product process is very energy consuming due to the different temperature requirements during the various steps. U.S. Pat. No. 4,316,956 provides a fermentation process for conversion of granular starch into ethanol. The European Patent EP0140410B2 provides an enzyme composition for starch hydrolysis. The object of the present invention is to provide improved processes for conversion of granular starch into alcohol products.

SUMMARY OF THE INVENTION

The present invention provides methods for producing an alcohol product from granular starch without prior gelatinization of said starch. Accordingly in a first aspect, the invention provides a process for production of an alcohol product comprising the steps of: (a) holding a slurry comprising water and granular starch at a temperature of 0° C. to 20° C. below the initial gelatinization temperature of said granular starch for a period of 5 minutes to 12 hours, and (b) fermenting the slurry of step (a) with a yeast at a temperature between 10° C. and 35° C. for a period of 20 to 250 hours to produce ethanol, wherein step (a) and (b) is performed in the presence of an acid alpha-amylase activity, a maltose generating enzyme activity and an alpha-glucosidase activity. The steps (a) and (b) are performed in the stated order; however, the process may comprise additional steps not specified in this description which are performed prior to, between or after any of steps (a) and (b).

Although not limited to any one theory of operation, the present invention, in particular, process step (a), is believed to result in swelling of starch granules enclosed in the plant cells resulting in the disruption of cell walls and release of the starch granules thereby rendering the starch granules more accessible to further hydration and the action of the enzymes. As hydration progresses through step (a), the acid alpha-amylase degrades the starch granules to produce dextrins, which are degraded by the maltose generating enzyme into maltose, and the maltose is finally degraded by alpha-glucosidase into glucose. This process continues during step (b) in which the glucose is continuously fermented to ethanol by the yeast, thereby maintaining the concentration of fermentable sugar at a relatively low concentration throughout the fermentation. Without being limited to any one theory of operation, it is believed that due to the low concentration of sugars present during fermentation, the production of glycerol by the yeast is decreased as there is a limited need for glycerol for osmoregulation. In this regard, the present invention may be used to produce an alcohol product which has a reduced glycerol and/or methanol content compared to conventional processes.

The present invention provides a less energy consuming alternative to conventional processes which must employ significant amounts of energy to gelatinize the starch slurry. other advantages of the present invention include, without limitation, the ability to employ a low pH throughout the process, thus reducing the risk of unwanted microbial growth, and reducing or eliminating the need for expensive equipment to gelatinize the starch, such as, jetting installations and steam plant equipment.

In a second aspect the present invention relates to an enzyme composition comprising an acid alpha-amylase activity, a maltose generating enzyme activity and an alpha-glucosidase activity, wherein an additional enzyme activity is present; said enzyme activity is selected from the list consisting of pullulanase, cellulase, xylanase and phytase.

In a third aspect the present invention relates to a use of the enzyme composition of the second aspect in an alcohol product process or a starch hydrolysis process.

In a fourth aspect the present invention relates to a use of an enzyme composition comprising an acid alpha-amylase activity, a maltose generating enzyme activity and an alpha-glucosidase activity, in an alcohol product process comprising hydrolysis of granular starch.

DETAILED DESCRIPTION OF THE INVENTION

The term "alcohol product" means a product comprising ethanol, e.g. fuel ethanol, potable and industrial ethanol. However, the alcohol product may also be a beer, which beer may be any type of beer. Preferred beer types comprise ales, stouts, porters, lagers, bitters, malt liquors, happoushu, high-alcohol beer, low-alcohol beer, low-calorie beer or light beer.

The term "granular starch" means raw uncooked starch, i.e. starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called gelatinization begins.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch is the temperature at which birefringence is lost in 5% of the starch granules using the method described by Gorinstein. S. and Lii. C., Starch/Stärke, Vol. 44 (12) pp. 461-466 (1992).

The polypeptide "homology" means the degree of identity between two amino acid sequences. The homology may suitably be determined by computer programs known in the art, such as, GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. The following settings for polypeptide sequence comparison are used: GAP creation penalty of 3.0 and GAP extension penalty of 0.1.

Acid Alpha-Amylases

The term "acid alpha-amylase" means an alpha-amylase (E.C. 3.2.1.1) which added in an effective amount has activity at a pH in the range of 3.0 to 7.0, preferably from 3.5 to 6.0, or more preferably from 4.0-5.0.

Any suitable acid alpha-amylase may be used in the present invention. A preferred acid alpha-amylase may be derived from a fungal or a bacterial strain.

A preferred acid fungal alpha-amylase is a Fungamyl-like alpha-amylase. In the present disclosure, the term "Fungamyl-like alpha-amylase" indicates an alpha-amylase which exhibits a high homology, i.e. more than 50%, 55%, 60%, 65%, 70%, 75%, 80%, 85% or even 90% homology to the amino acid sequence shown in SEQ ID No. 10 in WO96/23874 and/or as SEQ ID NO:5 herein. When used as a maltose generating enzyme fungal alpha-amylases may be added in an amount of 0.001-1.0 AFAU/g DS, preferably from 0.002-0.5 AFAU/g DS, preferably 0.02-0.1 AFAU/g DS.

Preferably the alpha-amylase is an acid alpha-amylase having at least 70%, preferably at least 75%, 80%, 85% or at least 90%, e.g. at least 95%, at least 97%, at least 98%, or at least 99% homology to the acid fungal alpha-amylase having the amino acid sequence set forth in SEQ ID NO:1. Most preferably the acid alpha-amylase is an acid fungal alpha-amylase having the amino acid sequence set forth in SEQ ID NO:1 or variants thereof having one or more amino acid residues which have been deleted, substituted and/or inserted compared to the amino acid sequence of SEQ ID NO:1; which variants have alpha-amylase activity.

Preferred acid bacterial alpha-amylase for use in the present invention may be derived from a strain of *B. licheniformis*, *B. amyloliquefaciens*, and *B. stearothenmophilus*. Also preferred are acid alpha-amylases having an amino acid sequence which has at least 50% homology, preferably at least 60%, 70%, 80%, 85% or at least 90%, e.g. at least 95%, 97%, 98%, or at least 99%, such as 100% homology to the sequences set forth in SEQ ID NO:2 or SEQ ID NO:3. Preferably the acid alpha-amylase used for the process of the invention is one of the acid alpha-amylase variants and hybrids described in WO96123874, WO97/41213, and WO99/19467, such as the *Bacillus stearothermnophilus* alpha-amylase (BSG alpha-amylase) variant having the following mutations delta(181-182)+N193F (also denoted I181*+G182*+N193F) compared to the wild type amino acid sequence set forth in SEQ ID NO:2. The acid bacterial alpha-amylase may also be a hybrid alpha-amylase comprising the 445 C-terminal amino acid residues of the *Bacillus licheniformis* alpha-amylase set forth in SEQ ID NO:3 and the 37 N-terminal amino acid residues of the alpha-amylase derived from *Bacillus amyloliquefaciens* set forth in SEQ ID NO:4, which may further have the substitutions G48A+T49I+G107A+H156Y+A181T+N190F+I201F+A209V+Q264S using the numbering in SEQ ID NO: 5 of WO 99/19467 shown herein as SEQ ID NO:3. Also preferred are alpha-amylase variants derived from *Bacillus amyloliquefaciens* and having at least 50% homology, such as at least 60%, at least 70%, at least 80%, or even 90% homology to the sequence set forth in SEQ ID NO:4. Especially preferred are variants having one or more of the mutations H154Y, A181T, N190F, A209V and Q264S and/or deletion of two residues between positions 176 and 179, preferably deletion of E178 and G179.

Preferred commercial compositions comprising acid alpha-amylase include Mycolase from DSM (Gist Brochades), BAN™, TERMAMYL™ SC, FUNGAMYL™, LIQUOZYME™ X and SAN™ SUPER, SAN™ EXTRA L (Novozymes A/S) and Clarase L-40,000, DEX-LO™, Spezyme FRED, SPEZYMET™, and SPEZYME™ DELTA AA (Genencor Int.).

Maltose Generating Enzymes

The maltose generating enzymes of the invention may be a maltogenic alpha-amylase, a beta-amylases or a fungal alpha-amylase.

Maltogenic alpha-amylases (glucan 1,4-alpha-maltohydrolase) are able to hydrolyse amylose and amylopectin to maltose in the alpha-configuration. Furthermore, a maltogenic alpha-amylase is able to hydrolyse maltotriose as well as cyclodextrins. Specifically contemplated maltogenic alpha-amylases may be derived from *Bacillus* sp., preferably from *Bacillus stearothermophilus*, most preferably from *Bacillus stearothermophilus* C599 such as the one described in EP120.693. This particular maltogenic alpha-amylase has the amino acid sequence shown as amino acids 1-686 of SEQ ID NO:1 in U.S. Pat. No. 6,162,628. A preferred maltogenic alpha-amylase has an amino acid sequence having at least 70% identity to amino acids 1-686 of SEQ ID NO:1 in U.S. Pat. No. 6,162,628, preferably at least 80%, at least 85%, at least 90%, at least 92%, at least 95%, at least 96%, at least 97%, at least 98%, or particularly at least 99%. Most preferred variants of the maltogenic alpha-amylase comprise the variants disclosed in WO99/43794.

Maltogenic alpha-amylases may be added in amounts of 0.01-40.0 MANU/g DS, preferably from 0.02-10 MANU/g DS, preferably 0.05-5.0 MANU/g DS.

Another maltose generating enzyme to be used in the processes of the invention may be a beta-amylase (E.C 3.2.1.2). Beta-amylase is the name traditionally given to exo-acting maltogenic amylases, which catalyze the hydrolysis of 1,4-alpha-glucosidic linkages in amylose, amylopectin and related glucose polymers.

Beta-amylases have been isolated from various plants and microorganisms (W. M. Fogarty and C. T. Kelly, Progress in Industrial Microbiology, vol. 15, pp. 112-115, 1979). These beta-amylases are characterized by having optimum temperatures in the range from 40° C. to 65° C. and optimum pH in the range from 4.5 to 7.0. Preferably the beta-amylase is derived from a filamentous fungus, such as a beta-amylase derived from *Rhizomucor pusilis*. Contemplated beta-amylase include the beta-amylase from barley Spezyme® BBA 1500, Spezyme® DBA and Optimalt™ ME, Optimal™ BBA from Genencor Int. as well as Novozym™ WBA from Novozymes A/S.

Another maltose generating enzyme to be used in the processes of the invention may be a fungal alpha-amylase (EC 3.2.1.1), such as a fungamyl-like alpha-amylase. In the present disclosure, the term "fungamyl-like alpha-amylase" indicates an alpha-amylase which exhibits a high homology, i.e. more than 50%, 55%, 60%, 65%, 70%, 75%, 80%, 85% or even 90% homology to the amino acid sequence shown in SEQ ID No. 10 in WO96/23874. When used as a maltose generating enzyme fungal alpha-amylases may be added in an amount of 0.001-1.0 AFAU/g DS, preferably from 0.002-0.5 AFAU/g DS, preferably 0.02-0.1 AFAU/g DS.

Alpha-Glucosidases

An alpha-glucosidase or maltase (EC 3.2.1.48) to be used in the processes of the invention may be derived from a microorganism, such as a bacteria or a fungus, or from a plant. Preferred is alpha-glucosidase of fungal origin such as an alpha-glucosidase derived from a yeast or from a filamentous fungi. Preferably the alpha-glucosidase is derived from a strain of *Candida* sp. such as a strain of *C. edax*, preferably the strain CBS 6461. Also preferred are the alpha-glucosidases derivable from a strain of *Pichia* sp., such as a strain of *P. amylophilia, P. missisippiensis, P. wicherhamil* and *P. rhodanensis*. Also contemplated are alpha-glucosidases derived from *Aspergillus* sp, such as *A.nidulans* (Kato et al. 2002, Appl Environ Microbiol. 68: 1250-1256), from *Rhizobium* sp. (Berthelot et al. 1999, Appl Environ Microbiol. 65: 2907-2911) or of plant origin such as derived from a cereal, such as from wheat, rye, barley corn or rice.

Preferred bacterial alpha-glucosidases include alpha-glucosidases derived from the genus *Bacillus*, such as from a strain of *Bacillus stearothemophilus*. Preferred are alpha-glucosidases having an amino acid sequence which has at least 50% homology, preferably at least 60%, 70%, 80%, 85% or at least 90%, e.g., at least 95%, 97%, 98%, or at least 99%, such as 100% homology to the mature part of the sequences set forth in SEQ ID NO:6 herein. A commercially available alpha-glucosidase contemplated is the *Bacillus stearothemophilus* alpha-glucosidase commercially available from SIGMA (Sigma cat. No. G3651). Alpha-glucosidases of plant origin may be derived from a cereal, such as from wheat, rye, barley corn or rice.

Alpha-glucosidases may be added in amounts of 0.1-10000 maltase units/kg DS, 1-1000 maltase units/kg DS, or more preferably 10-100 maltase units/kg DS, such as or more preferably 1-10 maltase units/kg DS.

Other Enzymes

A xylanase used according to the invention may be derived from any suitable organism, including fungal and bacterial organisms, such as *Aspergillus, Disporotrichum, Penicillium, Neurospora, Fusarum* and *Trichoderma*.

Xylanases may be added in amounts of 1-50000 FXU/kg DS, preferably 5-5000 FXU/kg DS, or more preferably 10-500 FXU/kg DS.

Preferred commercially available preparations comprising xylanase include SHEARZYME PLUS®, BIOFEED WHEAT®, CELLUCLAST®, ULTRAFLO®, VISCOZYME® (from Novozymes A/S) and SPEZYME® CP (from Genencor Int.).

The cellulase activity (E.C. 3.2.1.4) may be a cellulase of microbial origin, such as derivable from a strain of a filamentous fungus (e.g., *Aspergillus, Trichoderyna, Humicola, Fusarium*). Cellulases may be added in the amounts of 0.01-500000 EGU/kg DS, preferably from 0.1-10000 EGU/kg DS, preferably from 1-5000 EGU/kg DS, more preferably from 10-500 EGU/kg DS and most preferably from 100-250 EGU/kg DS.

Commercially available preparations comprising cellulase which may be used include SHEARZYME PLUS®, CELLUCLAST®, CELLUZYME®, CEREFLO® and ULTRAFLO®) (from Novozymes A/S), LAMINEX™ and SPEZYME® CP (from Genencor Int.) and ROHAMENT® 7069 W (from Röhm GmbH).

Another enzyme used in the process may be a debranching enzyme, such as a pullulanases (E.C. 3.2.1.41). Debranching enzyme may be added in effective amounts well known to the person skilled in the art.

In a first preferred embodiment of the first aspect, the invention provides a process for production of ethanol, comprising the steps of; (a) holding a slurry comprising water and granular starch at a temperature of 0° C. to 20° C. below the initial gelatinization temperature of said granular starch for a period of 5 minutes to 12 hours, (b) fermenting the slurry of step (a) with a yeast at a temperature between 10° C. and 35° C. for a period of 20 to 250 hours to produce ethanol; wherein step (a) and (b) is performed in the presence of an acid alpha-amylase activity, a maltose generating enzyme activity and an alpha-glucosidase activity.

The steps (a) and (b) are performed in the stated order, however, the process may comprise additional steps not specified in this description which are performed prior to, between or after any of steps (a) and (b).

In the first preferred embodiment of the first aspect the temperature under step (b) is between 28° C. and 36° C., preferably from 29° C. and 35° C., more preferably from 30° C. and 34° C., such as around 32° C. and the slurry is held in contact with the alpha-amylase, the glucoamylase and the yeast for a period of time sufficient to allow hydrolysis of the starch and fermentation of the released sugars during step (b), preferably for a period of 25 to 190 hours, preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours, such as 85 to 110 hours.

In a second preferred embodiment of the first aspect, the invention provides a process for production of a beer, comprising the steps of: (a) holding a slurry comprising water and granular starch at a temperature of 0° C. to 20° C. below the initial gelatinization temperature of said granular starch for a period of 5 minutes to 12 hours, (b) fermenting said with a yeast at a temperature between 10° C. and 18° C. for a period of 20 to 200 hours to produce ethanol; wherein step (a) and (b) is performed in the presence of an acid alpha-amylase activity, a maltose generating enzyme activity and an alpha-glucosidase activity. The steps (a) and (b) are performed in the stated order; however, the process may comprise additional steps not specified in this description which are performed prior to, between or after any of steps (a) and (b).

In the second preferred embodiment of the first aspect the temperature under step (b) is between 10° C. and 18° C., preferably from 11° C. and 17° C., more preferably from 12° C. and 16° C., such as between 13° C. and 15° C., e.g. around 14° C. and the slurry is held in contact with the acid alpha-amylase activity, a maltose generating enzyme activity and an alpha-glucosidase activity and the yeast for a period of time sufficient to allow hydrolysis of the starch and fermentation of the released sugars during step (c), preferably for a period of 100 to 230 hours, preferably from 150 to 210 hours, more preferably from 170 to 200 hours.

The acid alpha-amylase is added in an effective amount, which is a concentration of acid alpha-amylase sufficient for its intended purpose of converting the granular starch in the starch slurry to dextrins.

The maltose generating enzyme is added in an effective amount, which is a concentration of maltose generating enzyme sufficient for its intended purpose of converting the dextrins generated in the starch slurry to maltose.

The alpha-glucosidase is added in an effective amount, which is a concentration of alpha-glucosidase sufficient for its intended purpose of converting the maltose generated in the starch slurry to glucose.

In a preferred embodiment of the first aspect of the invention the step (a) and/or step (b) is performed in the presence of an additional enzyme activity selected from the list consisting of xylanase, cellulase and phytase. The additional enzyme is preferably added together with the alpha-amylase, the maltose generating enzyme and the alpha-glucosidase.

In a particular embodiment of the first aspect of the invention the step (a) and/or step (b) is performed in the presence or in the absence of a glucoamylase.

The enzyme activities may preferably be dosed in form of the composition of the second aspect of the invention.

In a preferred embodiment the starch slurry comprises water and 5-60% DS (dry solids) granular starch, preferably 10-50% DS granular starch, more preferably 15-40% DS, especially around 20-25% DS granular starch. The granular starch to be processed in the processes of the invention may in particular be obtained from tubers, roots, stems, cobs, legumes, cereals or whole grain. More specifically the granular starch may be obtained from corns, cobs, wheat, barley, rye, milo, sago, cassava, tapioca, sorghum, rice, peas, bean, banana or potatoes. Preferred are both waxy and non-waxy types of corn and barley. The granular starch to be processed may preferably comprising milled whole grain or it may be a more refined starch quality, preferably more than 90%, 95%, 97% or 99.5% pure starch. The raw material comprising the starch is preferably milled in order to open up the structure and allowing for further processing. Dry milling as well as wet milling may be used. When wet milling is applied it may be preceded by a soaking, or steeping step. Both dry and wet milling is well known in the art of alcohol manufacturing and is preferred for the processes of the invention. In the second embodiment of the first aspect of the invention wherein the alcohol product is a beer the granular starch may preferably comprise at least 10%, 20%, 30%, 40%, 50%, 60%, 70%, 80% or even at least 90% granular starch derived from malted cereals, e.g. barley malt.

The pH during step (a) and/or (b) is preferably in the range of 3.0 to 7.0, more preferably from 3.5 to 6.0, or most preferably from 4.0-5.0, such as from 4.3 to 4.6.

The slurry is held in contact with the enzymes at an elevated temperature but below the initial gelatinization temperature for a period of time effective to render the starch granules susceptible for enzymatic degradation (step b), preferably for a period of 5 minutes to 12 hours, preferably from 10 minutes to 6 hours, more preferably from 15 minutes to 3 hours, even more preferably from 20 minutes to 1½ hour, such as from 30 minutes to 1¼ hour, from 40 to 70 minutes, and even from 50 to 60 minutes. The temperature during step (a) should always be adjusted to be below the initial gelatinization temperature of the particular granular starch to be processed, and will typically be between 45° C. and 75° C. According to the invention step (a) is conducted at a temperature from 0° C. to 20° C., preferably from 0° C. to 15° C., more preferably from 0° C. to 10° C., or even more preferably from 0° C. to 5° C. below the initial gelatinization temperature of the particular starch to be processed. The actual temperature may be from 45° C. to 75° C., but is preferably from 55° C. to 65° C. Preferably the temperature at which step (a) is conducted is at least 45° C., 46° C., 47° C., 48° C., 49° C., 50° C., 51° C., 52° C., 53° C., 54° C., 55° C., 56° C., 57° C., 58° C. or preferably at least 55° C., and preferably the temperature is no more than 74° C., 73° C., 72° C., 71° C., 70° C., 69° C., 68° C., 67° C., 66° C., 65° C., 64° C., 63° C. or preferably no more than 62° C.

After being subjected to the process of the first aspect of the invention at least 85%, 86%, 87%, 88%, 89%, 90%, 91%, 92%, 93%, 94%, 95%, 96%, 97%, 98%, or preferably 99% of the dry solids of the granular starch is converted into ethanol.

The ethanol may optionally be recovered. The ethanol recovery may be performed by any conventional manner such as e.g. distillation and may be used as fuel ethanol and/or potable ethanol and/or industrial ethanol.

In a particularly preferred embodiment the granular starch to be processed is derived from dry or wet milled cereal, such as wheat, barley, rye, and/or corn, the starch slurry has a DS of 20-40 percent, the temperature during step (a) is from 50° C. to 60° C., such as 55° C., the duration of step (a) is from 30 minutes to 75 minutes, such as 60 minutes and step (b) is carried out for 60 to 90 hours.

In a preferred embodiment the composition of the second aspect of the invention an additional enzyme activity is present; said enzyme activity is selected from the list consisting of cellulase, xylanase and phytase.

Materials and Methods

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e. at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes ANS, Denmark, which folder is hereby included by reference.

Acid Alpha-Amylase Activity

When used according to the present invention the activity of any acid alpha-amylase may be measured in AFAU (Acid Fungal Alpha-amylase Units). Alternatively activity of acid alpha-amylase may be measured in AAU (Acid Alpha-amylase Units).

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard conditions/reaction conditions:

| Substrate: | Soluble starch. Concentration approx. 20 g DS/L. |
|---|---|
| Buffer: | Citrate, approx. 0.13 M, pH = 4.2 |
| Iodine solution: | 40.176 g potassium iodide + 0.088 g iodine/L |
| City water | 15°-20° dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in EP0140410B2, which disclosure is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 FAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

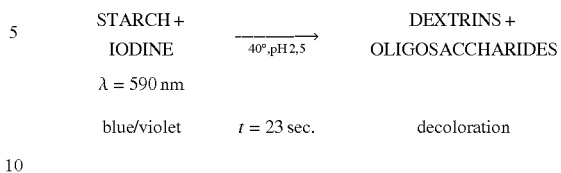

ALPHA-AMYLASE

STARCH + IODINE $\xrightarrow{40°,pH2,5}$ DEXTRINS + OLIGOSACCHARIDES $\lambda = 590$ nm blue/violet    $t = 23$ sec.    decoloration Standard conditions/reaction conditions:

| Substrate: | Soluble starch, approx. 0.17 g/L |
|---|---|
| Buffer: | Citrate, approx. 0.03 M |
| Iodine (I2): | 0.03 g/L |
| CaCl2: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Maltogenic Alpha-Amylase Activity (MANU)

One Maltogenic Amylase Novo Unit (MANU) is defined as the amount of enzyme which under standard will cleave one micro mol maltotriose per minute. The standard conditions are 10 mg/ml maltotriose, 37° C., pH 5.0, and 30 minutes reaction time. The formed glucose is converted by glucose dehydrogenase (GlucDH, Merck) to gluconolactone under formation of NADH, which is determined spectrophotometrically at 340 nm. A folder (EAL-SM-0203.01) describing this analytical method in more detail is available on request from Novozymes A/S, Denmark, which folder is hereby included by reference.

Beta-Amylase Activity (DP°)

The activity of SPEZYME® BBA 1500 is expressed in Degree of Diastatic Power (DP°). It is the amount of enzyme contained in 0.1 ml of a 5% solution of the sample enzyme preparation that will produce sufficient reducing sugars to reduce 5 ml of Fehling's solution when the sample is incubated with 100 ml of substrate for 1 hour at 20° C.

Pullulanase Activity (New Pullulanase Unit Novo (NPUN))

Pullulanase activity may be determined relative to a pullulan substrate. Pullulan is a linear D-glucose polymer consisting essentially of maltotriosyl units joined by 1,6-alpha-links. Endo-pullulanases hydrolyze the 1,6-alpha-links at random, releasing maltotriose, $6^3$-alpha-maltotriosyl-maltotriose, $6^3$-alpha-($6^3$-alpha-maltotriosyl-maltotriosyl)-maltotriose.

One new Pullulanase Unit Novo (NPUN) is a unit of endo-pullulanase activity and is measured relative to a Novozymes A/S Promozyme D standard. Standard conditions are 30 minutes reaction time at 40° C. and pH 4.5; and with 0.7% pullulan as substrate. The amount of red substrate degradation product is measured spectrophotometrically at 510 nm and is proportional to the endo-pullulanase activity in the sample. A folder (EB-SM.0420.02/01) describing this analytical method in more detail is available upon request to Novozymes A/S, Denmark, which folder is hereby included by reference.

Under the standard conditions one NPUN is approximately equal to the amount of enzyme which liberates reducing carbohydrate with a reducing power equivalent to 2.86 micromole glucose per minute.

Alpha-Lucosidase Activity

The alpha-glucosidase activity can be expressed in maltase units (g glucose formed/L maltase preparation/hour) as used in example 1-5. A maltase preparation is incubated at 60° C. in a 20% w/v maltose solution, in 50 mM citrate at pH=4.5 for 60 minutes (1 hour). The amount of glucose liberated is measured using the GOD-PERID assay, Boehringer Mannheim.

The alpha-glucosidase activity can alternatively be expressed in alpha-glucosidase units as used in example 6-9. One unit will liberate 1.0 micromole of D-glucose from p-nitrophenyl-alpha-D-glucoside per min at pH 6.8 at 37° C.

One maltase unit is approximately equal to 100 alpha-glucosidase units.

Xylanolvtic Activity

The xylanolytic activity can be expressed in FXU-units, determined at pH 6.0 with remazol-xylan (4-O-methyl-D-glucurono-D-xylan dyed with Remazol Brilliant Blue R, Fluka) as substrate.

A xylanase sample is incubated with the remazol-xylan substrate. The background of non-degraded dyed substrate is precipitated by ethanol. The remaining blue color in the supernatant (as determined spectrophotometrically at 585 nm) is proportional to the xylanase activity, and the xylanase units are then determined relatively to an enzyme standard at standard reaction conditions, i.e. at 50.0° C., pH 6.0, and 30 minutes reaction time.

A folder EB-SM-352.02/01 describing this analytical method in more detail is available upon request to Novozymes A/S, Denmark, which folder is hereby included by reference.

Cellulytic Activity

The cellulytic activity may be measured in endo-glucanase units (EGU), determined at pH 6.0 with carboxymethyl cellulose (CMC) as substrate. A substrate solution is prepared, containing 34.0 g/l CMC (Hercules 7 LFD) in 0.1 M phosphate buffer at pH 6.0. The enzyme sample to be analyzed is dissolved in the same buffer. 5 ml substrate solution and 0.15 ml enzyme solution are mixed and transferred to a vibration viscosimeter (e.g. MIVI 3000 from Sofraser, France), thermostated at 40° C. for 30 minutes. One EGU is defined as the amount of enzyme that reduces the viscosity to one half under these conditions. The amount of enzyme sample should be adjusted to provide 0.01-0.02 EGU/ml in the reaction mixture. The arch standard is defined as 880 EGU/g.

A folder EB-SM-0275.02/01 describing this analytical method in more detail is available upon request to Novozymes ANS, Denmark, which folder is hereby included by reference.

Phytase Activity

The phytase activity is measured in FYT units, one FYT being the amount of enzyme that liberates 1 micromole inorganic ortho-phosphate per min. under the following conditions: pH 5.5; temperature 37° C.; substrate: sodium phytate ($C_6H_{60}O_{24}P_6Na_{12}$) at a concentration of 0.0050 mole/l.

Enzymes Preparation

The following enzyme preparations were used:

An acid bacterial alpha-amylase; An enzyme preparations comprising a polypeptide with alpha-amylase activity (E.C. 3.2.1.1) derived from *B. stearothermophilus* and having the amino acid sequence disclosed as SEQ.NO:4 in WO99/19467. Activity: 120 KNU/g (density=1.20-1.25 g/mL).

An acid fungal alpha-amylase; an enzyme preparations derived from *Aspergillus niger* comprising acid fungal alpha-amylase and some glucoamylase. Activities: 114 AFAU/g, 25 AGU/g (density=1.2 g/mL).

An acid fungal alpha-amylase derived from *Aspergillus oryzae* having 800 FAU/g (density=1.25 g/mL). A maltogenic alpha-amylase with the amino acid sequence shown in SEQ ID No: 1 in WO9/943794 having 3200 MANU/g (1.25 g/mL).

A plant beta-amylase extracted from wheat grain, having 1250 DP/g (1.2 g/ml).

A fungal beta-amylase derived from *Rhizomucor pusilus*.

An alpha-glucosidase derived from *Candida edax*. Activity: 0.14 maltase units/g An enzyme preparation comprising xylanase and cellulase activities derived from *Trichoderma* and *Aspergillus*. Activity: 140 FXU/g+350 EGU/g (density=1.2 g/mL).

A pullulanase derived from *Bacillus acidopullulyticus* and described in EP 63,909.

Alpha-glucosidase BS: *Bacillus stearothemophilus* alpha-glucosidase available from SIGMA (Sigma cat. No. G3651). The enzyme has the amino-acid sequence shown in SEQ ID NO:6.

EXAMPLES

Traditional non-pressure batch cooking processes for production of potable alcohol is described in the Novozymes publication No. 2001-10782-01 entitled "Use of Novozymes enzymes in alcohol production".

A 20% D.S. slurry of the milled grain is made in room temperature (RT) tap water. For each parameter 2×250 g is portioned in 500 mL blue cap fermentation flasks. pH is adjusted to 4.5 using 6 N HCl. For the process of the invention enzymes are dosed according to the descriptions below and a pre-treatment is carried out for one hour at 55° C. in a shaking water bath. The flasks are now cooled to 32° C., 0.25 g dry bakers yeast is added to each flask (This corresponded to ~5-10 million vital cells/g mash) and the flasks are weighed. Incubation is performed in a shaking water bath preset at 32° C. Hereafter the flasks are equipped with air locks and fermentation at 32° C. is initiated in a shaking water bath.

A simultaneous saccharification and fermentation (SSF) process is carried out and continued for 72 hours. At 48 and 72 hours the flasks are weighed and $CO_2$ weight loss (g) measured for monitoring of the fermentation progress. The relationship used between amount of $CO_2$ loss and the weight of ethanol is: $CO_2$ loss (g)×1.045=EtOH (g).

Example 1

A milled whole barley grain slurry prepared as described above is held at 55° C., pH=4.5 in the presence of bacterial alpha-amylase, fungal alpha-amylase, and alpha-glucosidase for 60 minutes.

The following dosages can be used:

| Activity | Dosage/g dry matter grain |
| --- | --- |
| Bacterial alpha-amylase from *Bacillus* | 0.6 KNU |
| Fungal alpha-amylase from *A. niger* | 0.3 FAU |
| Alpha-glucosidase from *C. edax* | 0.01 maltase units |

The temperature is then adjusted to 32° C. and 3×250 g mash is portioned in 500 mL blue cap fermentation flasks with air locks. Fermentation is performed and monitored as described above.

Example 2

A milled whole barley grain slurry prepared as described above is held at 55° C., pH=4.5 in the presence of xylanase and cellulase, bacterial alpha-amylase, maltogenic alpha-amylase, and alpha-glucosidase for 60 minutes.

The following dosages can be used:

| Activity | Dosage/d dry matter grain |
|---|---|
| Trichoderma xylanase + Aspergillus cellulase preparation | 0.070 FXU/0.020 EGU |
| Bacterial alpha-amylase from *Bacillus* | 0.6 KNU |
| Maltogenic alpha-amylase | 0.3 MANU |
| Alpha-glucosidase from *C. edax* | 0.01 maltase units |

The temperature is then adjusted to 32° C. and 3×250 g mash is portioned in 500 mL blue cap fermentation flasks with air locks. Fermentation is performed and monitored as described above.

Example 3

A milled whole barley grain slurry prepared as described above is held at 55° C., pH=4.5 in the presence of acid fungal alpha-amylase, plant beta-amylase and alpha-glucosidase for 60 minutes.

The following dosages can be used:

| Activity | Dosage/g dry matter grain |
|---|---|
| Acid fungal alpha-amylase from *A. niger* | 0.5 AFAU |
| A plant beta-amylase from wheat | 0.15 DP |
| Alpha-glucosidase from *C. edax* | 0.01 maltase units |

The temperature is then adjusted to 32° C. and 3×250 g mash is portioned in 500 mL blue cap fermentation flasks with air locks. Fermentation is performed and monitored as described above.

Example 4

A milled whole wheat grain slurry prepared as described above is held at 55° C., pH=4.5 in the presence of acid fungal alpha-amylase, fungal beta-amylase, and alpha-glucosidase for 60 minutes.

The following dosages can be used:

| Activity | Dosage/g dry matter grain |
|---|---|
| Acid fungal alpha-amylase from *A. niger* | 0.5 AFAU |
| Fungal beta-amylase from *R. pusilus* | 0.3 MANU |
| Alpha-glucosidase from *C. edax* | 0.01 maltase units |

The temperature is then adjusted to 32° C. and 3×250 g mash is portioned in 500 mL blue cap fermentation flasks with air locks. Fermentation is performed and monitored as described above.

Example 5

A milled whole wheat grain slurry prepared as described above is held at 55° C., pH=4.5 in the presence of acid fungal alpha-amylase, maltogenic alpha-amylase, alpha-glucosidase and pullulanase for 60 minutes.

The following dosages can be used:

| Activity | Dosage/g dry matter grain |
|---|---|
| Acid fungal alpha-amylase from *A. niger* | 0.5 AFAU |
| Maltogenic alpha-amylase | 0.3 MANU |
| Alpha-glucosidase from *C. edax* | 0.01 maltase units |
| Pullulanase from *Bacillus* | 0.2 NPUN |

The temperature is then adjusted to 32° C. and 3×250 g mash is portioned in 500 mL blue cap fermentation flasks with air locks. Fermentation is performed and monitored as described above.

Example 6

A slurry of dry milled whole barley grain was held for 60 minutes at 55° C., pH=4.5 in the presence of bacterial alpha-amylase from *Bacillus*, fungal alpha-amylase from *A. oryzae* and alpha-glucosidase from *Candida edax*. The temperature was then adjusted to 32° C. and 2×250 g mash was portioned in 500 mL blue cap fermentation flasks with air locks. Fermentation was performed and monitored as described above.

Results of fermentation trial given in liter EtOH/100 kg mash dry matter

| Fermentation time, hours | Bacterial alpha-amylase 0.6 KNU(S)/g DS, Fungal alpha-amylase 0.3 FAU/g DS, Alpha-glucosidase 0.1 unit/g DS | Bacterial alpha-amylase 0.6 KNU(S)/g DS, Fungal alpha-amylase 0.3 FAU/g DS, Alpha-glucosidase 1 unit/g DS |
|---|---|---|
| 18.2 | 24.6 | 28.6 |
| 23.8 | 27.9 | 31.5 |
| 40.3 | 34.6 | 36.5 |
| 47.5 | 36.4 | 37.8 |
| 70.3 | 38.1 | 39.1 |

This example shows that the maltose forming enzyme system consisting of bacterial alpha-amylase and the fungal alpha-amylase is improved by increasing dosage of alpha-glucosidase. The starch content of barley is 54-65% and the ethanol yield is 34-41 L liters per 100 kg or 37-44 liters per 100 kg dry matter. Thus the trial shows that the ethanol yield obtained is close to the theoretically obtainable.

Example 7

A slurry of dry milled whole barley grain was held for 60 minutes at 55° C., pH=4.5 in the presence of bacterial alpha-amylase from *Bacillus*, maltogenic alpha-amylase and alpha-glucosidase from *Candida edax*. The temperature was then adjusted to 32° C. and 2×250 g mash was portioned in 500 mL blue cap fermentation flasks with air locks. Fermentation was performed and monitored as described above.

| Results of fermentation trial given in litre EtOH/100 kg mash dry matter | | |
|---|---|---|
| Fermentation time, hours | Fungal alpha-amylase 0.6 KNU(S)/g DS, Maltogenic alpha-amylase 0.3 MANU/g DS, Alpha-glucosidase 0.1 units/g DS | Fungal alpha-amylase 0.6 KNU(S)/g DS, Maltogenic alpha-amylase 0.3 MANU/g DS, Alpha-glucosidase 1 units/g DS |
| 18.2 | 24.7 | 29.2 |
| 23.8 | 28.0 | 31.7 |
| 40.3 | 34.5 | 36.5 |
| 47.5 | 36.3 | 37.8 |
| 70.3 | 38.4 | 39.3 |

This example shows that the maltose forming enzyme system consisting of bacterial alpha-amylase and the maltogenic alpha-amylase is improved by increasing dosage of alpha-glucosidase. The ethanol yield obtained is close to the theoretically obtainable.

Example 8

A slurry of dry milled whole barley grain was held for 60 minutes at 55° C., pH=4.5 in the presence of bacterial alpha-amylase from *Bacillus*, plant beta-amylase and alpha-glucosidase from *Candida edax*. The temperature was then adjusted to 32° C. and 2×250 g mash was portioned in 500 mL blue cap fermentation flasks with air locks. Fermentation was performed and monitored as described above.

| Results of fermentation trial given in litre EtOH/100 kg mash dry matter | | |
|---|---|---|
| Fermentation time, hours | Bacterial alpha-amylase 0.6 KNU(S)/g DS, Plant beta-amylase 0.15 DP/g DS, Alpha-glucosidase 0.1 units/g DS | Bacterial alpha-amylase 0.6 KNU(S)/g DS, Plant beta-amylase 0.15 DP/g DS, Alpha-glucosidase 1 units/g DS |
| 18.2 | 24.6 | 29.7 |
| 23.8 | 27.8 | 32.4 |
| 40.3 | 34.5 | 37.5 |
| 47.5 | 36.2 | 38.7 |
| 70.3 | 37.9 | 40.1 |

This example shows that the maltose forming enzyme system consisting of bacterial alpha-amylase and the plant beta-amylase is improved by increasing dosage of alpha-glucosidase (Alpha-glucosidase). The ethanol yield obtained is close to the theoretically obtainable.

Example 9

A 12-14% D.S. slurry of the milled wheat grain was made in room temperature (RT) tap water. For each parameter 2×250 g was portioned in 500 mL blue cap fermentation flasks. pH was adjusted to 6.0. For the process of the invention was used Alpha-amylase from *Bacillus*, a plant beta-amylase, alpha-glucosidase from *Bacillus stearothermnophilus* (Sigma-product no. G3651). Enzymes were dosed according to the descriptions below and a pre-treatment was carried out for 60 minutes at 55° C. in a shaking water bath. The flasks were cooled to 32° C., 0.25 9 dry bakers yeast (corresponding to 10 million vital cells/g mash) was added to each flask, the flasks were equipped with air locks, and weighed. The flasks were incubated in a shaking water bath preset at 32 IC and a simultaneous saccharification and fermentation (SSF) process step was carried out for approximately 67 hours. The flasks were weighed and $CO_2$ weight loss (g) measured for monitoring of the fermentation progress. The relationship used between amount of $CO_2$ loss and the weight of ethanol is: $CO_2$ loss (g)×1.045=EtOH (g). The yield of ethanol was calculated as:

Litre $EtOH$/100 kg mash dry matter =

$$\frac{\text{Weight loss (g)} \times 1.045}{0.79\,(\text{g/mL}) \times 250 \times 20\%\,\text{dry matter}} \times 100$$

% Ethanol in the fermented mash was determined by HPLC using Ion moderated partitioning.

| Results of fermentation trials. Enzymes: Bacterial alpha-amylase from *Bacillus* 0.15 KNU, Plant beta-amylase 0.15 DP and Alpha-glucosidase from *Bacillus stearothermophilus* 1 or 2 Alpha-glucosidase units. Fermented starch by mass balance calculations. | | | |
|---|---|---|---|
| | Yield, liter ETOH/ 100 kg mash DS | % EtOH | % Fermented starch |
| Alpha-glucosidase 1 unit | 38.3 | 3.4 | 82.1 |
| Alpha-glucosidase 2 units | 40.4 | 4.5 | 86.6 |

Increasing the dosage of Alpha-glucosidase improves the obtained yield of ethanol and the percentage of fermented starch based on mass balance calculations after the fermentation. The starch content of ground wheat is 5862% and the ethanol yield is practically 36-39 L liters per 100 kg or 39-42 liters per 100 kg dry matter. Thus the trial shows that the ethanol yield obtained is close to the usually practically obtained even the percentage of fermented starch has not reached completeness. Higher yields may be obtained including a pullulanase in enzyme combination.

The invention claimed is:

1. A process for production of an alcohol product comprising the steps of:
   (a) holding a slurry comprising water and granular starch at a temperature of 0° C. to 20° C below the initial gelatinization temperature of said granular starch for a period of 5 minutes to 12 hours,
   (b) fermenting the slurry of step (a) with a yeast at a temperature between 10° C. and 35° C. for a period of 20 to 250 hours to produce ethanol,
   wherein steps (a) and (b) are performed in the presence of an acid alpha-amylase activity, a maltose generating enzyme activity and an alpha-glucosidase activity.

2. The process according to claim 1, comprising recovering the ethanol.

3. The process according to claim 1, wherein the product is an ethanol product selected from the group consisting of fuel ethanol, potable ethanol and industrial ethanol.

4. The process according to claim 1, wherein the temperature under step (b) is between 29° C. and 35° C.

5. The process according to claim 1, wherein the alcohol product is a beer.

6. The process according to claim 1, wherein the temperature under step (b) is between 11° C. and 17° C.

7. The process according to claim 1, wherein the acid alpha-amylase is an acid fungal alpha-amylase.

8. The process according to claim 1, wherein the acid fungal alpha-amylase is obtained from a strain of *Aspergillus*.

9. The process according to claim 1, wherein the acid fungal alpha-amylase is obtained from a strain of *Aspergillus niger*.

10. The process according to claim 1, wherein the acid alpha-amylase is an acid bacterial alpha-amylase.

11. The process according to claim 1, wherein the acid alpha-amylase is derived from a strain of *B. licheniformis, B. amyloliquefaciens*, or *B. stearothermophilus* alpha-amylase.

12. The process according to claim 1, wherein the acid bacterial alpha-amylase is derived from a strain of *B. licheniformis, B. amyloliquefaciens*, or *B. stearothermophilus* alpha-amylase.

13. The process according to claim 1, wherein the maltose generating enzyme activity is a maltogenic alpha-amylase.

14. The process according to claim 1, wherein the maltose generating enzyme activity is a beta-amylase.

15. The process according to claim 1, wherein the alpha-glucosidase activity is derived from a strain of *Candida* sp.

16. The process according to claim 1, wherein the alpha-glucosidase activity is derived from a strain of *Bacillus* sp.

17. The process according to claim 1, wherein step (a) and (b) are performed in the presence of a pullulanase.

18. The process according to claim 1, wherein step (a) or step (b) is performed in the presence of an enzyme activity selected from the group consisting of xylanase, cellulase and phytase.

19. The process of claim 1, wherein the starch slurry has 5-60% DS granular starch.

20. The process of claim 1, wherein the pH during step (a) or (b) is in the range of 3.0 to 7.0.

21. The process of claim 1, wherein the granular starch is obtained from tubers, roots, stems, fruits, seeds or whole grain, or cereal, corn, cobs, wheat, barley, rye, milo, sago, cassava, man ioc, tapioca, sorghum, rice or potatoes.

22. The process of claim 1, wherein the granular starch is obtained from dry milling or wet milling of whole grain.

23. The process according to claim 1, wherein the temperature under step (a) is from 45° C. to 75° C.

24. A process for production of an alcohol product comprising the steps of:
   (a) holding a slurry comprising water and granular starch at a temperature of 0° C. to 20° C. below the initial gelatinization temperature of said granular starch,
   (b) fermenting the slurry of step (a) with a yeast at a temperature between 10° C. and 35° C.,
wherein steps (a) and (b) are performed in the presence of an acid alpha-amylase activity, a maltose generating enzyme activity and an alpha-glucosidase activity.

* * * * *

UNITED STATES PATENT AND TRADEMARK OFFICE
CERTIFICATE OF CORRECTION

PATENT NO.       : 7,579,177 B2                                        Page 1 of 1
APPLICATION NO. : 10/558552
DATED            : August 25, 2009
INVENTOR(S)      : Olsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this

Fourteenth Day of September, 2010

David J. Kappos
*Director of the United States Patent and Trademark Office*